US011826101B2

United States Patent
Charles (10) Patent No.: US 11,826,101 B2
(45) Date of Patent: Nov. 28, 2023

(54) SCENE CAMERA SYSTEMS AND METHODS FOR VITREORETINAL SURGERY

(71) Applicant: Alcon Inc., Fribourg (CH)

(72) Inventor: Steven T. Charles, Germantown, TN (US)

(73) Assignee: Alcon Inc., Fribourg (CH)

( * ) Notice: Subject to any disclaimer, the term of this patent is extended or adjusted under 35 U.S.C. 154(b) by 546 days.

(21) Appl. No.: 16/941,289

(22) Filed: Jul. 28, 2020

(65) Prior Publication Data
US 2021/0038070 A1    Feb. 11, 2021

Related U.S. Application Data

(60) Provisional application No. 62/883,298, filed on Aug. 6, 2019.

(51) Int. Cl.
*A61B 3/08*        (2006.01)
*A61B 3/00*        (2006.01)
(Continued)

(52) U.S. Cl.
CPC .............. *A61B 3/08* (2013.01); *A61B 3/0033* (2013.01); *A61B 3/0058* (2013.01); *A61F 9/007* (2013.01);
(Continued)

(58) Field of Classification Search
CPC ............ G02B 2027/0138; G02B 27/01; G02B 2027/0178; G02B 27/017; G02B 2027/0187; G02B 2027/014; G02B 27/0172; G02B 27/0093; G02B 27/28; G02B 30/24; G02B 2027/0123; G02B 2027/0127; G02B 2027/0132; G02B 2027/0174; G02B 27/00; G02B 27/0176; G02B 27/18; G02B 27/20; G02B 30/25; G02B 30/27; A61B 3/0025; A61B 3/0033;
(Continued)

(56) References Cited

U.S. PATENT DOCUMENTS 8,510,166 B2 *  8/2013  Neven ................ G06Q 30/0242
                                                 705/14.69
2015/0077543 A1 *  3/2015  Kerr ..................... H04N 5/33
                                                   348/135
(Continued)

FOREIGN PATENT DOCUMENTS

WO    2016013634 A1    1/2016
WO    2016018488 A2    2/2016
WO    2017063714 A1    4/2017

*Primary Examiner* — Brandi N Thomas (57) ABSTRACT

The present disclosure provides a scene camera system including a scene camera that includes a lens and may detect light reflected off an exterior of an eye into the lens and send a signal corresponding to the detected light to a processor. The system further includes a main camera that may detect light reflected off an interior structure of the eye and send a signal corresponding to the detected light to the processor. The system also includes an image processing system including the processor that executes instructions to produce a scene camera digital image of the eye and a main camera digital image of the eye. The system further includes a multiple picture-in-picture display that displays the scene camera digital image of the eye and the main camera digital image of the eye concurrently.

18 Claims, 7 Drawing Sheets

(51) Int. Cl.
*A61F 9/007* (2006.01)
*G02B 27/01* (2006.01)
*H04N 5/33* (2023.01)
*H04N 25/76* (2023.01)

(52) U.S. Cl.
CPC ............. *G02B 27/01* (2013.01); *H04N 5/33* (2013.01); *H04N 25/76* (2023.01); *G02B 2027/0138* (2013.01)

(58) Field of Classification Search
CPC .......... A61B 3/0058; A61B 3/08; A61B 3/14; A61B 3/113; A61B 3/00; A61B 3/024; A61B 3/12; H04N 5/33; H04N 25/76; H04N 7/18; H04N 13/00; H04N 13/204; H04N 13/239; H04N 13/246; H04N 13/337; H04N 13/341; H04N 13/344; H04N 23/00; H04N 23/90; H04N 1/2116; H04N 1/32128; H04N 13/305; H04N 13/31; H04N 13/359; H04N 13/361; H04N 13/398; H04N 2101/00; H04N 2201/3225; H04N 2201/3276; H04N 23/50; H04N 23/56; H04N 23/631; H04N 23/67; H04N 7/15

See application file for complete search history.

(56) References Cited

U.S. PATENT DOCUMENTS

2015/0177504 A1* 6/2015 Bickert ................. G02B 21/34
 348/80
2016/0379593 A1 12/2016 Borenstein \* cited by examiner

SCENE CAMERA SYSTEMS AND METHODS FOR VITREORETINAL SURGERY

TECHNICAL FIELD

The present disclosure relates to vitreoretinal surgery and surgical equipment, and more specifically, to a scene camera system to improve visualization during vitreoretinal surgery and associated methods.

BACKGROUND

Ophthalmic surgery is surgery performed on the eye or any part of the eye. Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

One type of ophthalmic surgery, vitreoretinal surgery, encompasses various delicate procedures involving internal portions of the eye, such as the vitreous humor, the retina, and the vitreoretinal membrane. Different vitreoretinal surgical procedures are used, sometimes with lasers, to improve visual sensory performance in the treatment of many eye diseases, including epimacular membrane, diabetic retinopathy, vitreous hemorrhage, macular hole, detached retina, and complications of cataract surgery, among others.

During ophthalmic surgery, such as vitreoretinal surgery, an ophthalmologist typically uses an analog surgical microscope with oculars to view a magnified image of the eye undergoing surgery. More recently, vitreoretinal surgeons may use an ocular-free digital image visualization system during vitreoretinal surgery. This system may include a three-dimensional (3D) high dynamic range (HDR) camera that allows the surgeon to view the retina on a display screen using polarized glasses. This provides relief from having to view the surgery using oculars and allows others in the operating room to see exactly as the surgeon does. The system also allows for improved images under high magnification, and increased depth of field compared to an analog surgical microscope, which provide improved visualization of the eye.

SUMMARY

The present disclosure provides a scene camera system including a scene camera that includes a lens and detects light reflected off an exterior of an eye into the lens and sends a signal corresponding to the detected light to a processor. The scene camera system further includes a main camera that detects light reflected off an interior structure of the eye and sends a signal corresponding to the detected light to the processor. The scene camera system also includes an image processing system including the processor and that executes instructions to produce a scene camera digital image of the eye and a main camera digital image of the eye. The scene camera system further includes a multiple picture-in-picture display that displays the scene camera digital image of the eye and the main camera digital image of the eye concurrently.

The scene camera system and its methods of use may include the following additional features: i) the lens may be a fixed focal length lens, an opto-mechanical focus lens, a manual focus lens, or any combination thereof; ii) the scene camera may detect light reflected off the exterior of the eye using an image sensor that is a charge-coupled device (CCD) sensor, a complementary metal-oxide semiconductor (CMOS) sensor, a monochrome image sensor, a color image sensor, or any combination thereof; iii) the scene camera may be an infrared scene camera that may detect infrared light reflected off the exterior of the eye into the lens, the scene camera digital image of the eye may be an infrared lower magnification digital image of the eye and the main camera digital image of the eye may be a higher magnification digital image of the eye, and the multiple picture-in-picture display may display the infrared lower magnification digital image of the eye and the higher magnification digital image of the eye concurrently; iv) the infrared scene camera may have a fixed focal length lens, an opto-mechanical focus lens, a manual focus lens, or any combination thereof; v) the infrared scene camera may further include an active infrared illuminator; vi) the infrared lower magnification digital image of the eye may be produced without use of an external illumination source; vii) the infrared scene camera may detect infrared light reflected off the exterior of the eye using an infrared image sensor that is an active infrared image sensor, an uncooled infrared image sensor, an infrared sensitive CMOS sensor, or any combination thereof; viii) the multiple picture-in-picture display may be displayed on a digital display, a screen, a head up display, a head mounted display, or any combination thereof; ix) the scene camera may be mounted by a ball and socket friction mount, a gooseneck, or a malleable mount; x) the scene camera may be mounted on the main camera; xi) the scene camera may have a view path at an oblique angle to a surgical view path; xii) the system may be a component of a NGENUITY® 3D Visualization System (Novartis AG Corp., Switzerland); xiii) the scene camera digital image of the eye may be a lower magnification digital image of the eye and the main camera digital image of the eye may be a higher magnification digital image of the eye; xiv) the scene camera may be a stereo scene camera that may detect light reflected off the exterior of the eye into a right lens and a left lens, the processor may execute instructions to produce a lower magnification right-eye-view image and a lower magnification left-eye-view image, the processor may execute instructions to combine the lower magnification right-eye-view image and the lower magnification left-eye view image to produce a stereoscopic lower magnification digital image of the eye, the scene camera digital image of the eye may be the stereoscopic lower magnification digital image of the eye and the main camera digital image of the eye may be a higher magnification digital image of the eye, and the multiple picture-in-picture display may display the stereoscopic lower magnification digital image of the eye and the higher magnification digital image of the eye concurrently; xv) the right lens and the left lens may be fixed focal length lenses; xvi) the scene camera may be an infrared stereo scene camera further able to detect infrared light reflected off the exterior of the eye into a right lens and a left lens, the processor may further execute instructions to produce an infrared lower magnification right-eye-view image and an infrared lower magnification left-eye-view image, and to combine the infrared lower magnification right-eye-view image and the infrared lower magnification left-eye view image to produce a stereoscopic infrared lower magnification digital image of the eye, the scene camera digital image of the eye may be the stereoscopic infrared lower magnification digital image of the eye and the main camera digital image of the eye may be a higher magnification digital image of the eye, and the multiple picture-in-picture display may display the stereoscopic infrared lower magnification digital image of the eye and the higher magnification digital image of the eye concurrently; xvii) the infrared stereo scene camera may include the right lens and the left lens that may be fixed focal length lenses.

The present disclosure further provides a method for performing a surgical task at lower magnification while preserving surgeon dark adaptation during vitreoretinal surgery by using an infrared stereo scene camera to capture a stereoscopic infrared lower magnification digital image of an exterior of eye without an external illumination source; using a main camera to capture a higher magnification digital image of an interior structure of the eye; using a multiple picture-in-picture display to view the stereoscopic infrared lower magnification digital image of the exterior of the eye and the higher magnification digital image of the interior structure of the eye concurrently; and performing a surgical task at lower magnification without shifting a visualization system from viewing the higher magnification digital image of the interior of the eye to viewing the stereoscopic infrared lower magnification digital image of the exterior of the eye and without use of an external illumination source. The surgical task may be suturing a wound, visualizing tools, visualizing cannulas, inserting tools into cannulas, inserting an infusion cannula, or any combination thereof.

Aspects of the scene camera system and its methods of use may be combined with one another unless clearly mutually exclusive. In addition, the additional features of the scene camera system and its associated methods described above may also be combined with one another unless clearly mutually exclusive.

BRIEF DESCRIPTION OF THE DRAWINGS

For a more complete understanding of the present disclosure and its features and advantages, reference is now made to the following description, taken in conjunction with the accompanying drawings, which are not to scale, in which like numerals refer to like features, and in which.

DETAILED DESCRIPTION

The present disclosure provides systems including a scene camera to improve visualization for vitreoretinal surgery and associated methods.

Vitreoretinal surgeons face unique challenges when visualizing the internal portions of the eye. Vitreoretinal surgery often involves viewing the retina, macula, vitreous humor, or other inner areas of the eye at a higher magnification in a narrow field of view. These inner areas of the eye are illuminated, often by an endoilluminator light source placed in the eye. In order to improve the view of illuminated areas in the eye, low light conditions are present outside of the eye. However, during vitreoretinal surgery, the surgeon may need to perform a surgical task outside the eye or in an area of the eye not near the retina. For example, the surgeon may need to insert or remove instruments, usually through an incision, cannula, or port in the eye. These surgical tasks are performed at lower magnification and may involve viewing the eye with a wide field of view. In such a view, only the low light conditions are available, which can make it difficult to perform the task. However, if the level of light outside the eye is increased by an external illumination source to facilitate performing a task outside the eye or in an area of the eye not near the retina, then when the level of light outside the eye is lowered again, it takes time for the surgeon's own eyes to readapt to the low light conditions and the level of illumination provided within the eye, prolonging the surgery.

Surgical tasks that may involve performing a surgical task at lower magnification, and may also involve use of an external illumination source, include suturing a wound, where the surgeon may need to visualize pulling the suture tight by viewing a lower magnification image of the eye. Other surgical tasks include visualizing tools and cannulas, and inserting tools into cannulas, especially curved tools such as a flexible laser probe or scissors. In other situations, an infusion cannula inserted into the eye for supplying fluid may be inadvertently part-way pulled out during surgery, potentially resulting a loss of pressure inside the eye. In addition, removal of dislocated intraocular lenses or intraocular foreign bodies involve observing a lower magnification image of the eye.

The systems and methods disclosed herein may improve visualization during vitreoretinal surgery by preventing disruptive processes involved with performing a surgical task at lower magnification. For example, the systems and methods disclosed herein may avoid the need to increase the level of light outside the eye using an external illumination source when performing a surgical task on the exterior of the eye, outside the eye or in a region of the eye not near the retina. The systems and methods disclosed herein may also allow the surgeon to view a part of the eye at higher magnification and a part of the eye at lower magnification without needing to adjust a microscope. The systems and methods disclosed herein may improve visualization during vitreoretinal surgery as compared to current systems and methods by i) providing a lower magnification digital image of the eye during surgery without adjustment of a surgical microscope (this image may be constant or presented upon user demand); ii) providing a stereoscopic lower magnification digital image of the eye during surgery; and iii) providing a lower magnification digital image of the eye without use of an external illumination source during surgery.

The systems and methods of the present disclosure may improve visualization during vitreoretinal surgery as compared to current systems and methods by including a scene camera system that may prevent shifting a visualization system from viewing a higher magnification digital image of the eye to viewing a lower magnification digital image of the eye when performing a surgical task at lower magnification. The scene camera system may also improve visualization during vitreoretinal surgery by allowing the surgeon to remove tools from or insert tools into the eye without use of an external illumination source, thereby preserving surgeon dark adaptation. The scene camera system described herein may be a component of a Digitally Assisted Vitreoretinal Surgery ("DAVS") system, or may be a component of the NGENUITY® 3D Visualization System (Novartis AG Corp., Switzerland). The scene camera system may also improve visualization during anterior segment surgery.

Current systems and methods for digital visualization during vitreoretinal surgery do not include a scene camera system. Instead, they require the surgeon to zoom the visualization system out from viewing a higher magnification image of the eye to a lower magnification image of the eye when a surgical task is performed at lower magnification. This is especially problematic if the surgeon wears presbyopic correction and is using a visualization system that has an optimal viewing distance, because the microscope or camera may need to be refocused every time the surgeon shifts the visualization system to view the exterior of the eye, which is away from retina.

Current systems and methods also rely on use of an external illumination source to perform surgical tasks at lower magnification. This disrupts surgeon dark adaptation and may prolong the surgery.

The scene camera system described herein may provide a lower magnification digital image of the eye to improve visualization during vitreoretinal surgery by including a scene camera. The scene camera may allow a surgeon to avoid shifting a visualization system from viewing a higher magnification digital image of the eye to viewing a lower magnification digital image of the eye when performing a surgical task at lower magnification. A lower magnification may be in the range of 2×-4× magnification of the eye.

The scene camera may include a lens, which may be a fixed focal length lens, an opto-mechanical focus lens, a manual focus lens, or any combination thereof. The fixed focal length lens may provide a fixed field of view for a duration of time, such as the duration of the surgical procedure or a portion of the surgical procedure. The focal length of the lens may be in the range of 150-200 mm, or may be any focal length appropriate to obtain a field of view wide enough for a suitable view of the eye. This may provide a wide field of view of the surgical procedure, which may be a view including the eye and optionally also at least one surgical instrument inserted into the eye. The distance between the scene camera and the eye of the patient may be altered to change the field of view of the scene camera. The scene camera may be mounted off axis to the surgical view path that provides an image of the interior of the eye at higher magnification. The scene camera may allow a surgeon to have a view path at an oblique angle to the surgical view path, which may be inclined toward the surgeon with respect to a vertical surgical view path. This may allow a surgeon to look past a retinal visualization system, which may be a Binocular Indirect Ophthalmo-Microscope (BIOM®; OCULUS Surgical, Inc., USA) or a RESIGHT® (Carl Zeiss Meditec AG, Germany), without moving it, changing the focal plane, shifting the retinal visualization system from viewing a higher magnification digital image of the eye to viewing a lower magnification digital image of the eye, or without use of an external illumination source. The scene camera may be attached to a microscope, or may be attached to the visualization system. The scene camera may extend below the microscope or visualization system and may almost touch the eye. The scene camera may provide a scene camera digital image of the eye, which may be a lower magnification digital image of the eye. The lower magnification digital image of the eye may include a view of the eye and optionally also at least one surgical instrument inserted into the eye.

The scene camera may be a monochrome camera, or it may be a color camera, and it may include a monochrome image sensor or a color image sensor. The image sensor may be a charge-coupled device (CCD) sensor or a complementary metal-oxide semiconductor (CMOS) sensor. The scene camera may include an image sensor with or without a color filter array, for example a Bayer filter. The scene camera may detect light reflected off the exterior of the eye into a lens and send a signal corresponding to the detected light to a processor. The processor may be part of an image processing system.

In the scene camera system described herein, the scene camera may be utilized in conjunction with a main camera. The main camera, when used together with the scene camera, may allow a surgeon to perform a surgical task at lower magnification without shifting the visualization system from viewing a higher magnification digital image of the eye to viewing a lower magnification digital image of the eye. The main camera may provide a main camera digital image of the eye, which may be a higher magnification digital image of the eye. The higher magnification digital image of the eye may include digital images of the macula, vitreous humor, retina, vitreoretinal pathology, or other areas of the eye, or it may simply provide a digital image of higher magnification than the lower magnification digital image of the eye provided by the scene camera. The main camera may also provide a stereoscopic main camera digital image of the eye, which may be a stereoscopic higher magnification digital image of the eye.

The main camera may be a digital camera, an HDR camera, a 3D camera, or any combination thereof. The main camera may also be a camera coupled to a surgical microscope. The main camera may replace oculars on a surgical microscope, and may be a fifth generation image capture module (ICM5) 3D surgical camera. The scene camera may be mounted on the main camera or may be mounted on another part of a visualization system. The scene camera may be mounted off axis to the surgical view path. The scene camera may be mounted by a ball and socket friction mount, a gooseneck, or a malleable mount.

The main camera may be a monochrome camera, or it may be a color camera, and it may include a monochrome image sensor or a color image sensor. The main camera may also be a pair of cameras for 3D visualization. The image sensor may be a charge-coupled device (CCD) sensor or a complementary metal-oxide semiconductor (CMOS) sensor. The main camera may include an image sensor with or without a color filter array, for example a Bayer filter. The main camera may detect light reflected off an interior structure of the eye and send a signal corresponding to the detected light to a processor. The processor may be part of an image processing system.

The scene camera system may use a visible light illumination source for the main camera, which may be an endoilluminator. The visible light illumination source may illuminate the interior structures of the eye. The visible light illumination source may alternatively be included in the scene camera system, and may be part of the main camera. The visible light illumination source may include a white light source, a white light-emitting diode (LED), an infrared LED, or any other suitable light source. The visible light illumination source may be configured such that it does not interfere with the dark adaptation of the surgeon during vitreoretinal surgery.

The scene camera system described herein may include a display. The display may include any type of screen or projector able to display a digital image of the eye with sufficient resolution to be usable in ophthalmic surgery. For instance, it may include any type of screen or projector used in connection with ophthalmic surgery, including displays of the type used in conventional vitreoretinal surgical systems that present digital images. The display may display a single image, or two images for stereoscopic viewing. The display may be a digital display, a screen, a head up display, a head mounted display, or any combination thereof. The display may be a flat panel display or an ultra-high-definition 3D flat panel display. The display may be a 3D organic light-emitting diode (OLED) surgical display. The images displayed on display may be viewed through a pair of passive, circular polarized glasses. The display may be a component of a Digitally Assisted Vitreoretinal Surgery ("DAVS") system, or may be a component of a NGENUITY® 3D Visualization System (Novartis AG Corp., Switzerland). The display may display a digital image captured by the scene camera, or may display a digital image captured by the main camera, or may display a digital image captured by the scene camera and a digital image captured by the main camera concurrently.

The scene camera system described herein may include a display that is a multiple picture-in-picture display. The multiple picture-in-picture display may include at least two input signals, which may be from the scene camera and the main camera. The multiple picture-in-picture display may display at least two digital images concurrently. The multiple picture-in-picture display may display the scene camera digital image of the eye and the main camera digital image of the eye concurrently. The multiple picture-in-picture display may display more than two images concurrently. On other examples, the multiple picture-in-picture display may display an intraoperative optical coherence tomography (OTC) image or an endoscope image.

The multiple picture-in-picture display may display a main image and a picture-in-picture sub image. The main image may be displayed in full screen, and the picture-in-picture sub image may be displayed in an inset position. The inset position may be located at the top, bottom, left, right, or any combination thereof, of the multiple picture-in-picture display. The multiple picture-in-picture display may display a higher magnification digital image of the eye in full screen and a lower magnification digital image of the eye in the inset position, or may display a lower magnification digital image of the eye in full screen and a higher magnification digital image of the eye in the inset position. The multiple picture-in-picture display may display a lower magnification digital image of the eye and a higher magnification digital image of the eye concurrently. This may avoid shifting a visualization system from viewing a higher magnification digital image of the eye to viewing a lower magnification digital image of the eye when performing a surgical task at lower magnification.

The multiple picture-in-picture display may include a controller to control whether a digital image of the eye is displayed as a main image or as a picture-in-picture sub image, and may control the size, position, relative placement, brightness, resolution, color, or any combination thereof of the digital image. The multiple picture-in-picture display may also include a controller to turn a lower magnification digital image of the eye on or off. The multiple picture-in-picture display may display a digital image of the eye in color or in monochrome. The multiple picture-in-picture display may be a digital display, a screen, a head up display, a head mounted display, or any combination thereof, and may also include multiple displays.

The scene camera system described herein may provide a stereoscopic lower magnification digital image of the eye to improve external visualization during vitreoretinal surgery by including a stereo scene camera. The stereo scene camera may provide a stereoscopic lower magnification digital image of the eye by capturing two separate lower magnification digital images of the eye that may simulate a lower magnification right-eye-view of the eye and a lower magnification left-eye-view of the eye. A lower magnification right-eye-view image may be combined with a lower magnification left-eye-view image to give a stereoscopic lower magnification digital image of the eye. The stereoscopic lower magnification digital image of the eye may be displayed on the multiple picture-in-picture display. The stereoscopic lower magnification digital image of the eye may allow performing a surgical task at lower magnification. A stereo scene camera may include a right lens and a left lens, and may include a separate image sensor for the right lens and a separate image sensor for the left lens, or alternatively two sensors and a common lens. The right lens and the left lens of the stereo scene camera may be positioned appropriately such that a lower magnification right-eye-view image and a lower magnification left-eye-view image are obtained. The distance between the right lens and the left lens of the stereo scene camera may be approximately the intra-ocular distance, or may be approximately 5-10 mm. The right lens and left lens may be included in the same stereo scene camera. The stereo scene camera may be mounted on the main camera, or may be mounted on another part of a visualization system. The stereo scene camera may be mounted off axis to the surgical view path. The stereo scene camera may be mounted by a ball and socket friction mount, a gooseneck, or a malleable mount.

Alternatively, the right lens of the stereo scene camera may be included in a separate right scene camera and the left lens of the stereo scene camera may be included in a separate left scene camera. Right scene camera and left scene camera may be mounted such that in combination they are equivalent to a stereo scene camera. Right scene camera and left scene camera may be mounted on the main camera, or may be mounted on another part of a visualization system. Right scene camera and left scene camera may be mounted off axis to the surgical view path. Right scene camera and left scene camera may be mounted by a ball and socket friction mount, a gooseneck, or a malleable mount.

The scene camera system described herein may provide a lower magnification digital image of the eye without use of an external illumination source to improve visualization during vitreoretinal surgery by including an infrared scene camera. The infrared scene camera may be a scene camera that detects infrared light, which may be light having a wavelength in the range of 0.7-1000 microns. The infrared scene camera may detect infrared light reflected off an exterior of an eye and send a signal corresponding to the detected infrared light to a processor to produce an infrared lower magnification digital image of the eye. The infrared scene camera may provide an infrared lower magnification digital image of the eye by using an active infrared illuminator, or by detecting passive infrared light radiating from objects in its field of view. The infrared lower magnification digital image of the eye captured by the infrared scene camera may be displayed on the multiple picture-in-picture display. The infrared scene camera may provide an infrared lower magnification digital image of the eye without use of an external illumination source. This may preserve the dark adaptation of the surgeon when performing a surgical task at lower magnification.

The infrared scene camera may be a component of the scene camera system in addition to the scene camera, or may replace the scene camera. The infrared scene camera may be a scene camera that includes at least one infrared image sensor. The infrared image sensor may be a photodetector that detects infrared light, and may be an active infrared image sensor, an uncooled infrared image sensor, an infrared sensitive CMOS sensor, or any combination thereof. Alternatively, the infrared scene camera may be an infrared stereo scene camera, and may have at least two infrared image sensors. If the infrared scene camera is an infrared stereo scene camera, it may provide a stereoscopic infrared lower magnification digital image of the eye.

Figure 1:
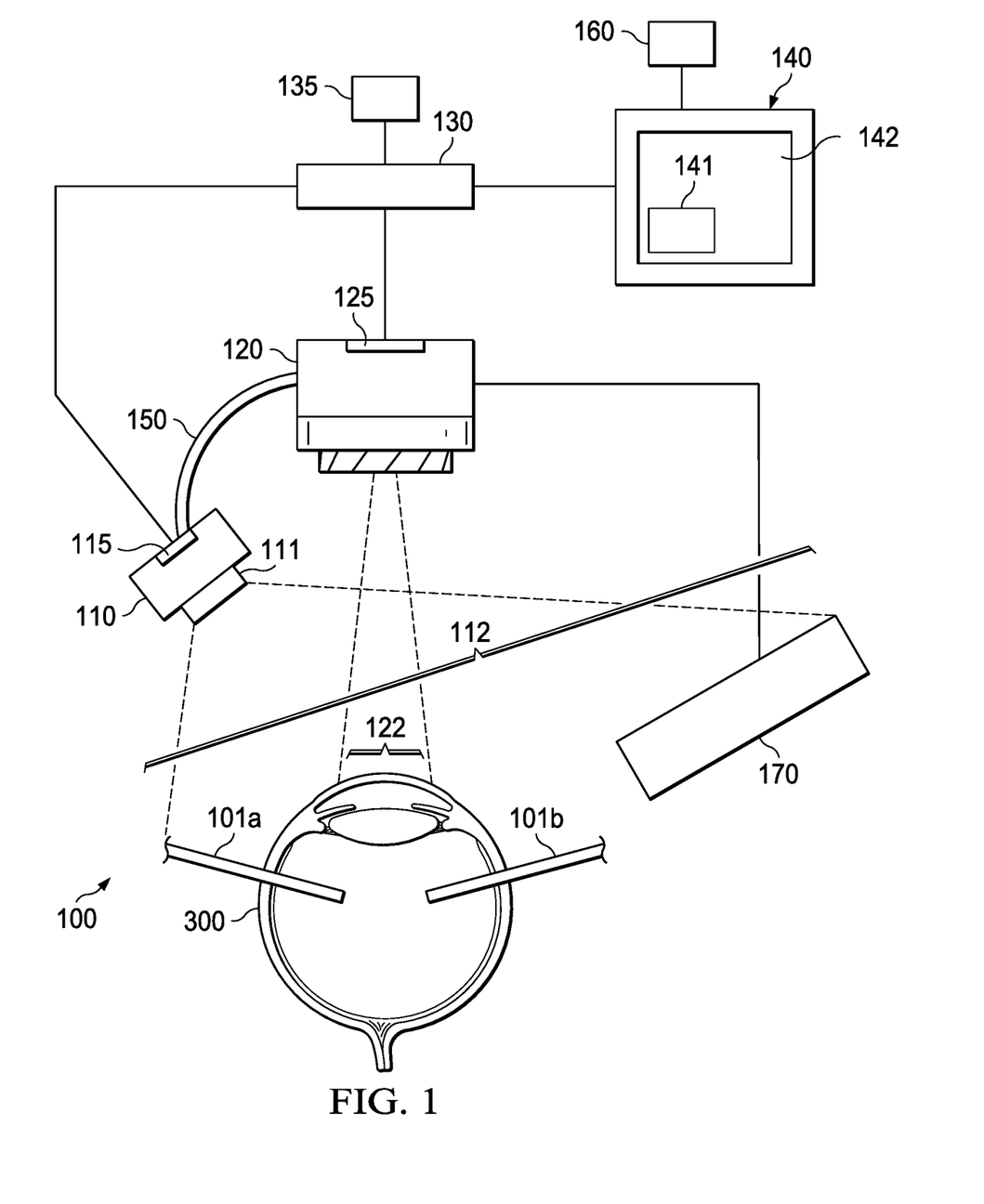
FIG. 1 is a schematic representation of a scene camera system, including a scene camera, a main camera, an image processing system, and a multiple picture-in-picture display.

Referring now to FIG. 1, scene camera system 100 includes scene camera 110, main camera 120, image processing system 130, and multiple picture-in-picture display 140. Scene camera system 100 may provide a lower magnification digital image of the eye to improve visualization during vitreoretinal surgery by allowing a surgeon to perform a surgical task at lower magnification. Scene camera 110 may capture a scene camera digital image of the eye, which may be lower magnification digital image of the eye 141. Lower magnification digital image of the eye 141 may be an image corresponding to field of view 112, which may be a wide field of view. Field of view 112 may include eye 300, and may include surgical instruments 101a and 101b. Surgical instruments 101a and 101b may be cannulas, or may be other surgical tools used in vitreoretinal surgery. Scene camera 110 may include lens 111. Lens 111 may be a fixed focal length lens that may give field of view 112. Lens 111 may have a short focal length that may give a wide field of view. Lens 111 may have a focal length in the range of 12-35 mm, or may have any focal length appropriate to obtain a suitable field of view 112. Field of view 112 may be fixed for the duration of a surgical procedure. Lens 111 may also be an opto-mechanical focus lens, a manual focus lens, or any combination thereof.

Scene camera 110 may include scene camera image sensor 115, which may be a charge-coupled device (CCD) sensor or a complementary metal-oxide semiconductor (CMOS) sensor. Scene camera 110 may be a monochrome camera, or may be a color camera, and scene camera image sensor 115 may be a monochrome image sensor or may be a color image sensor. Scene camera image sensor 115 may be an image sensor with a color filter array, for example a Bayer filter, or may be an image sensor without a color filter array.

Scene camera system 100 may also include main camera 120, which may be utilized in conjunction with scene camera 110 to allow a surgeon to perform a surgical task at lower magnification without shifting a visualization system from viewing a higher magnification digital image of the eye to viewing a lower magnification digital image of the eye. Main camera 120 may capture a main camera digital image of the eye, which may be higher magnification digital image of the eye 142. Higher magnification digital image of the eye 142 may be an image with field of view 122, which may be a narrow field of view. Field of view 122 may include a close-up view of eye 300, and may include a higher magnification view of the macula, vitreous humor, or other areas of eye 300. Field of view 122 may be a field of view that is narrower than field of view 112, and may correspond to a digital image of eye 300 that has a higher magnification than lower magnification digital image of the eye 141. Main camera 120 may also be configured to provide a stereoscopic higher magnification digital image of eye 300 (not shown).

Main camera 120 may be a digital camera, an HDR camera, a 3D camera, or any combination thereof. Main camera 120 may also be a camera coupled to a microscope. Main camera 120 may replace the oculars on a microscope, and may be a fifth generation image capture module (ICM5) 3D surgical camera. Scene camera 110 may be mounted on main camera 120 by mount 150, and may be mounted off axis to the surgical view path. Scene camera 110 may have a view path at an oblique angle to the surgical view path. Mount 150 may be a ball and socket friction mount, a gooseneck, or a malleable mount.

Main camera 120 may include main camera image sensor 125, which may be a charge-coupled device (CCD) sensor or a complementary metal-oxide semiconductor (CMOS) sensor. Main camera 120 may be a monochrome camera, or may be a color camera, and main camera image sensor 125 may be a monochrome image sensor or may be a color image sensor. Main camera image sensor 125 may be an image sensor with a color filter array, for example a Bayer filter, or may be an image sensor without a color filter array. Scene camera system 100 may also include visible light illumination source 170 as a visible light illumination source for main camera 120. Visible light illumination source 170 may be an endoilluminator, and may include a xenon source, a white LED light source, or any other suitable visible light source. Visible light illumination source 170 may illuminate the interior structures of the eye.

Digital images captured by scene camera image sensor 115 and main camera image sensor 125 may be processed by image processing system 130. Image processing system 130 may include processor 135. Scene camera 110 may detect light reflected off the exterior of eye 300 into lens 111 using scene camera image sensor 115, which may send a signal corresponding to the detected light to processor 135. Main camera 120 may detect light reflected off an interior structure of eye 300 using main camera image sensor 125, which may send a signal corresponding to the detected light to processor 135. Processor 135 may execute instructions to produce a scene camera digital image of the eye, which may be lower magnification digital image of the eye 141, and a main camera digital image of the eye, which may be higher magnification digital image of the eye 142.

Processor 135 may include, for example a microprocessor, a microcontroller, a digital signal processor (DSP), a field-programmable gate array (FPGA), an application specific integrated circuit (ASIC), or any other digital or analog circuitry configured to interpret and/or execute program instructions and/or process data. Processor 135 may also include any physical device able to store and run algorithms to produce the image of eye 300. Although processor 135 is depicted separately from scene camera image sensor 115 and main camera image sensor 125, they may be part of a single physical device, such as a single camera, a single computer or a set of integrated circuits. Processor 135 may interpret and/or execute program instructions and/or process data stored in a memory. The memory may be configured in part or whole as application memory, system memory, or both. The memory may include any system, device, or apparatus configured to hold and/or house one or more memory modules. Each memory module may include any system, device or apparatus configured to retain program instructions and/or data for a period of time (e.g., computer-readable media). The various servers, electronic devices, or other machines described may contain one or more similar such processors or memories for storing and executing program instructions for carrying out the functionality of the associated machine.

Scene camera system 100 may include multiple picture-in-picture display 140. Multiple picture-in-picture display 140 may display at least two digital images concurrently. Multiple picture-in-picture display 140 may display the scene camera digital image of the eye, which may be lower magnification digital image of the eye 141, and the main camera digital image of the eye, which may be higher magnification digital image of the eye 142, concurrently. This may prevent shifting a visualization system from viewing a higher magnification image of the eye to viewing a lower magnification image of the eye for performing a surgical task at lower magnification, which may include inserting or removing surgical instruments 101a and 101b from eye 300, or for example inserting tools into cannulas, checking, reinserting or inserting the infusion cannula or suturing a wound.

Figure 2:
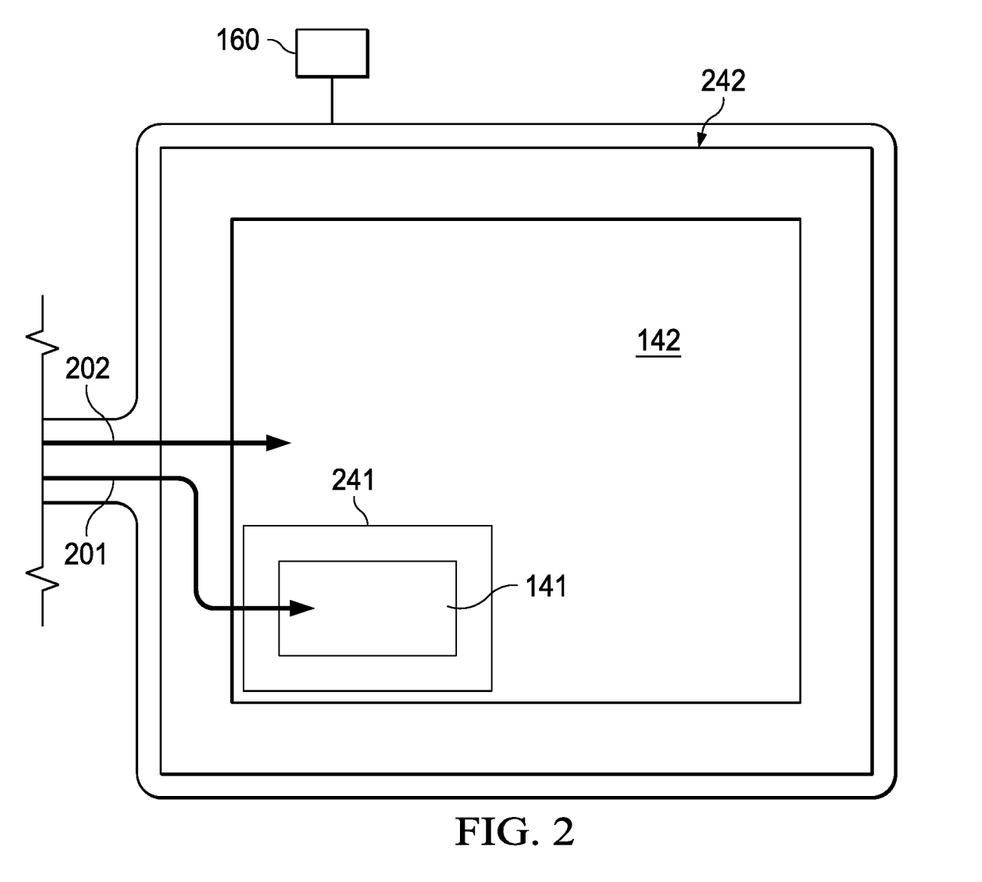
FIG. 2 is a schematic representation of a multiple picture-in-picture display.

Multiple picture-in-picture display 140 in scene camera system 100 may include at least two input signals, which may be scene camera input signal 201 and main camera input signal 202 as depicted in FIG. 2. Scene camera input signal 201 may be instructions from processor 135 to display the scene camera digital image of the eye, which may be lower magnification digital image of the eye 141. Main camera input signal 202 may be instructions from processor 135 to display the main camera digital image of the eye, which may be higher magnification digital image of the eye 142. Digital images of the eye displayed by multiple picture-in-picture display 140 may be displayed in color or in monochrome. Multiple picture-in-picture display 140 may display a main image, which may be displayed in full screen position 242 and a picture-in-picture sub image, which may be displayed in inset position 241. Multiple picture-in-picture display 140 may display lower magnification digital image of the eye 141 as a picture-in-picture sub image in inset position 241 and higher magnification digital image of the eye 142 as a main image in full screen position 242 as shown, or may display lower magnification digital image of the eye 141 as a main image in full screen position 242 and higher magnification digital image of the eye 142 as a picture-in-picture sub image in inset position 241 (not shown). Inset position 241 may be located at the top, bottom, left, right, or any combination thereof, of multiple picture-in-picture display 140. Inset position 241 may be a size that is smaller than full screen position 242. Alternatively, multiple picture-in-picture display may display lower magnification digital image of the eye 141 and higher magnification digital image of the eye 142 side-by-side in full screen (not shown).

Multiple picture-in-picture display 140 may include a controller 160. Controller 160 may control the digital images of the eye displayed in full screen position 242 and inset position 241, and may control the size, position, relative placement, brightness, resolution, color, or any combination thereof of the digital images. Controller 160 may also control if a single image or multiple images are displayed by multiple picture-in-picture display 140. Processor 135 may vary the on/off status or luminous flux or wavelengths of light of visible light illumination source 170, for example in response to input from controller 160, to improve visibility of eye 300 as viewed on multiple picture-in-picture display 140. Multiple picture-in-picture display 140 may also display a digital image of eye 300 generated by processor 135 or another processor and other information generated by processor 135 or another processor. Such information may include graphic or textual information, such as surgical parameters, warnings, graphs, color coding or augmented reality information. Multiple picture-in-picture display 140 may be a digital display, a screen, a head up display, a head mounted display, or any combination thereof, and may also include multiple displays.

Figure 3:
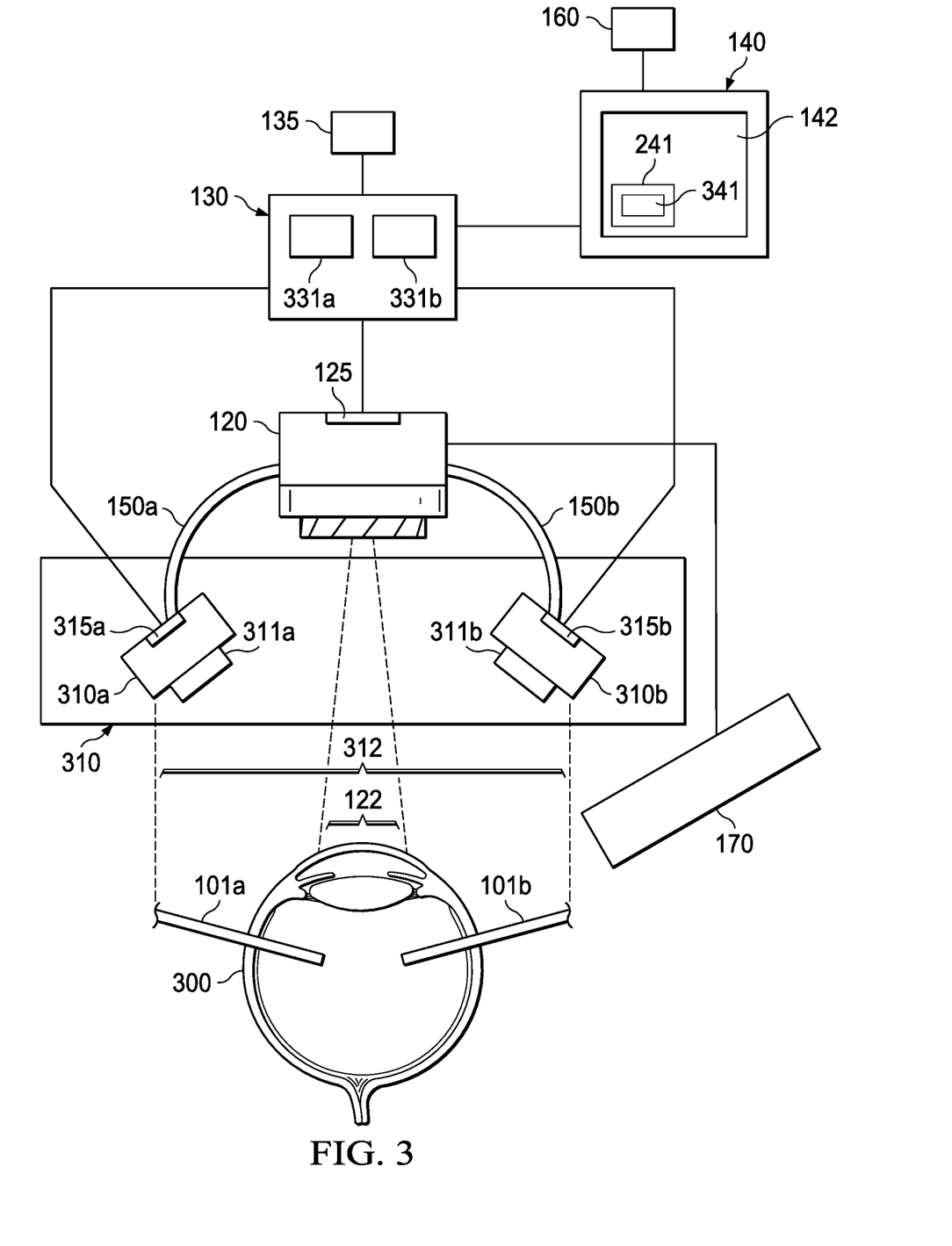
FIG. 3 is a schematic representation of a scene camera system, including a stereo scene camera, a main camera, an image processing system, and a multiple picture-in-picture display.

Scene camera system 100 may include stereo scene camera 310 as depicted in FIG. 3. Stereo scene camera 310 may include right lens 311a and left lens 311b. Right lens 311a and left lens 311b may be fixed focal length lenses that may give field of view 312. Right lens 311a and left lens 311b may have a short focal length that may give a wide field of view. Right lens 311a and left lens 311b may have a focal length in the range of 150-200 mm, or may have any focal length appropriate to obtain a suitable field of view 312. Field of view 312 may be fixed for the duration of a surgical procedure.

Stereo scene camera 310 may provide stereoscopic lower magnification digital image of the eye 341 during surgery. Stereo scene camera 310 may detect light reflected off the exterior of eye 300 into right lens 311a and left lens 311b and send a signal corresponding to the detected light to processor 135. Processor 135 may execute instructions to produce lower magnification right-eye-view image 331a and lower magnification left-eye-view image 331b. Processor 135 may execute instructions to combine lower magnification right-eye-view image 331a and lower magnification left-eye-view image 331b to produce stereoscopic lower magnification digital image of the eye 341. Stereoscopic lower magnification digital image of the eye 341 may be displayed by multiple picture-in-picture display 140, and may be displayed in inset position 241. Multiple picture-in-picture display 140 may display stereoscopic lower magnification digital image of the eye 341 and a main camera digital image of the eye, which may be higher magnification digital image of the eye 142, concurrently. Stereoscopic lower magnification digital image of the eye 341 may allow a surgeon to perform a surgical task at lower magnification, which may include inserting or removing surgical instruments 101a and 101b from eye 300, or for example inserting tools into cannulas, or suturing a wound.

Right scene camera 310a may include right lens 311a and left scene camera 310b may include left lens 311b. Right scene camera 310a and left scene camera 310b may be two separate physical cameras. Alternatively, right scene camera 310a and left scene camera 310b may be combined into a single physical stereo scene camera. Right lens 311a and left lens 311b may be fixed focal length lenses, which may have the same focal length. Right scene camera 310a may include right image sensor 315a and left scene camera 310b may include left image sensor 315b.

Right image sensor 315a and left image sensor 315b may be charge-coupled device (CCD) sensors or complementary metal-oxide semiconductor (CMOS) sensors. Right image sensor 315a and left image sensor 315b may be monochrome image sensors or may be color image sensors. Right image sensor 315a and left image sensor 315b may be image sensors with a color filter array, for example a Bayer filter, or may be image sensors without a color filter array.

Right lens 311a may be positioned appropriately such that right scene camera 310a may detect light reflected off the exterior of eye 300 into lens 311a using right image sensor 315a, which may send a signal corresponding to the detected light to processor 135 to produce lower magnification right-eye-view image 331a. Left lens 311b may be positioned appropriately such that left scene camera 310b may detect light reflected off the exterior of eye 300 into left lens 311*b* using left image sensor 315*b*, which may send a signal corresponding to the detected light to processor 135 to produce lower magnification left-eye-view image 331*b*. Processor 135 may execute instructions to combine lower magnification right-eye-view image 331*a* and lower magnification left-eye-view image 331*b* to produce stereoscopic lower magnification digital image of the eye 341. The distance between right lens 311*a* and left lens 311*b* may be approximately the intra-ocular distance, or may be approximately 5-10 mm. Stereo scene camera 310 may be mounted on main camera 120, and may be mounted off axis to the surgical view path. Stereo scene camera 310 may be mounted by a ball and socket friction mount, a gooseneck, or a malleable mount.

Alternatively, if right scene camera 310*a* and left scene camera 310*b* are two separate physical cameras, they may be mounted separately on main camera 120. Right scene camera 310*a* may be mounted on main camera 120 by mount 150*a*, and left scene camera 310*b* may be mounted on main camera 120 by mount 150*b*. Right scene camera 310*a* and left scene camera 310*b* may be mounted off axis to the surgical view path. Mounts 150*a* and 150*b* may be ball and socket friction mounts, goosenecks, or malleable mounts.

Figure 4:
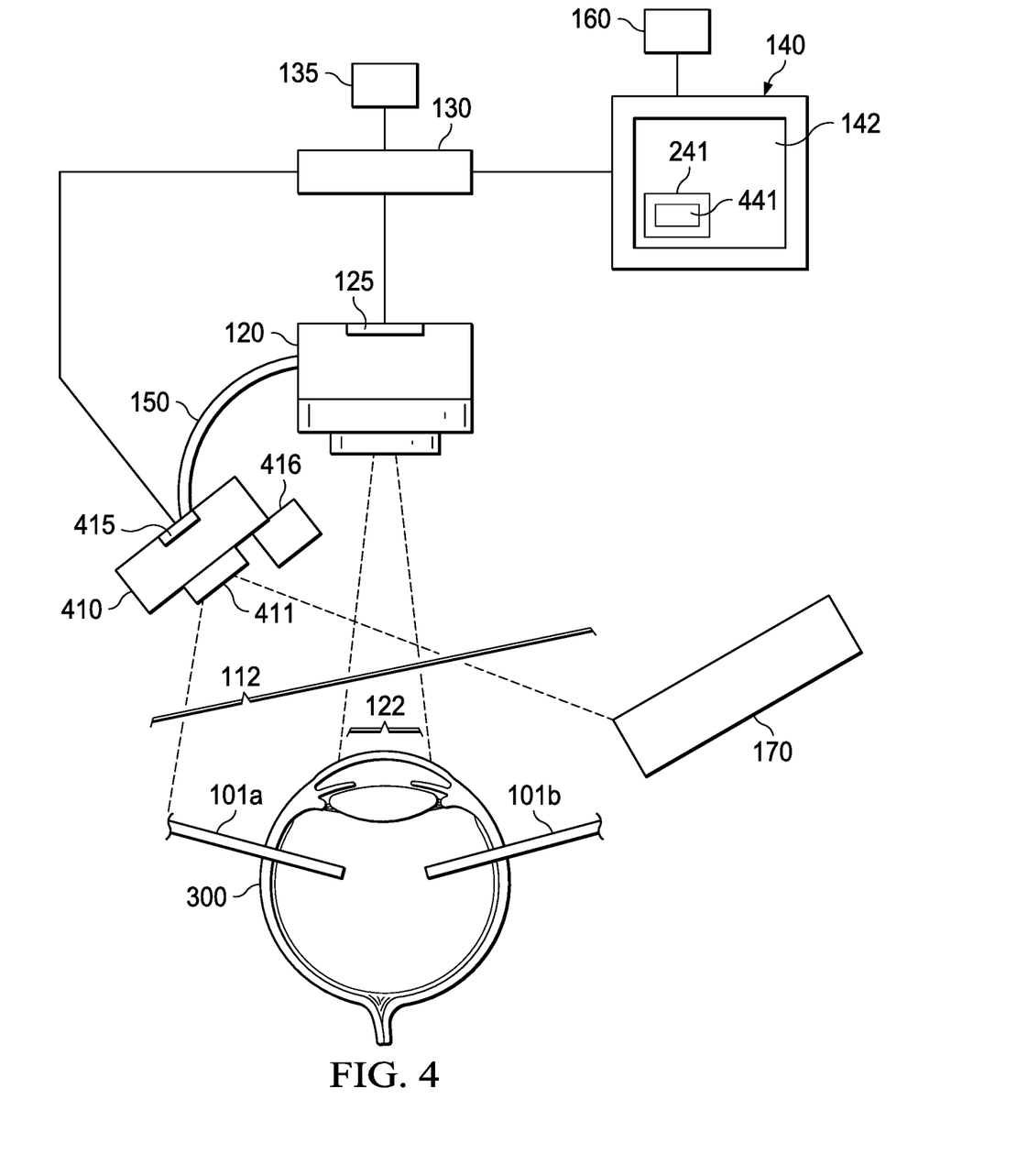
FIG. 4 is a schematic representation of a scene camera system, including an infrared scene camera, a main camera, an image processing system, and a multiple picture-in-picture display.

Scene camera system 100 may include infrared scene camera 410 as depicted in FIG. 4. Infrared scene camera 410 may be a scene camera that detects infrared light, which may be light having a wavelength in the range of 0.7-1000 microns. Infrared stereo camera 410 may include at least one infrared image sensor 415. Infrared image sensor 415 may be a photodetector that detects infrared light. Infrared image sensor 415 may be an active infrared image sensor, an uncooled infrared image sensor, or may be an infrared sensitive CMOS sensor. Infrared scene camera 410 may detect infrared light reflected off the exterior of eye 300 into lens 411 and send a signal to a processor 135 to produce infrared lower magnification digital image of the eye 441. Lens 411 may be a fixed focal length lens, an opto-mechanical focus lens, a manual focus lens, or any combination thereof. Infrared lower magnification digital image of the eye 441 may be displayed by multiple picture-in-picture display 140, and may be displayed in inset position 241. Multiple picture-in-picture display 140 may display infrared lower magnification digital image of the eye 441 and a main camera digital image of the eye, which may be higher magnification digital image of the eye 142, concurrently. Infrared scene camera 410 may detect reflected infrared light, may detect emitted infrared light, or any combination thereof. Infrared scene camera 410 may include active infrared illuminator 416, which may emit infrared light in the thermal part of the infrared spectrum. Infrared scene camera 410 may use infrared image sensor 415 to detect infrared light emitted by active infrared illuminator 416 and reflected off the exterior of eye 300.

Digital images captured by infrared scene camera image sensor 415 may be sent to image processing system 130. Image processing system 130 may include processor 135. Infrared scene camera 410 may detect infrared light reflected off the exterior of eye 300 into lens 411 using infrared image sensor 415, which may send a signal corresponding to the detected infrared light to processor 135. Processor 135 may execute instructions to produce an infrared scene camera digital image of the eye, which may be infrared lower magnification digital image of the eye 441.

Infrared scene camera 410 may produce infrared lower magnification digital image of the eye 441 without use of an external illumination source. This may preserve the dark adaptation of the surgeon when performing a surgical task at lower magnification, which may include inserting or removing surgical instruments 101*a* and 101*b* from eye 300, or for example inserting tools into cannulas.

Infrared scene camera 410 may be mounted on main camera 120 by mount 150, and may be mounted off axis to the surgical view path. Mount 150 may be a ball and socket friction mount, a gooseneck, or a malleable mount.

Figure 5:
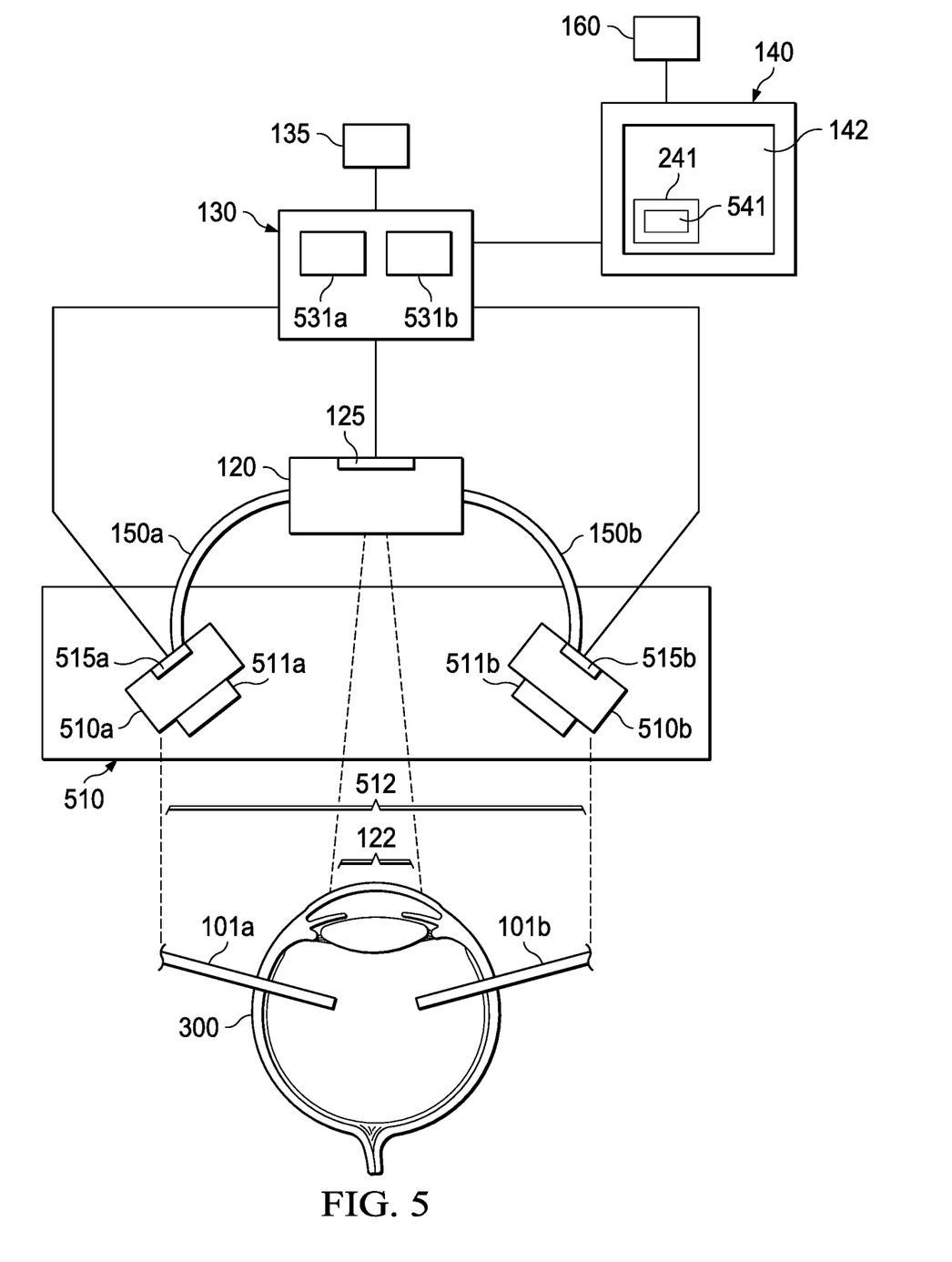
FIG. 5 is a schematic representation of a scene camera system, including an infrared stereo scene camera, a main camera, an image processing system, and a multiple picture-in-picture display.

Scene camera system 100 may include infrared stereo scene camera 510 as depicted in FIG. 5. Infrared stereo scene camera 510 may include right lens 511*a* and left lens 511*b*. Right lens 511*a* and left lens 511*b* may be fixed focal length lenses that may give field of view 512. Right lens 511*a* and left lens 511*b* may have a short focal length that may give a wide field of view. Right lens 511*a* and left lens 511*b* may have a focal length in the range of 12-35 mm, or may have any focal length appropriate to obtain a suitable field of view 512. Field of view 512 may be fixed for the duration of a surgical procedure.

Infrared stereo scene camera 510 may provide stereoscopic infrared lower magnification digital image of the eye 541. Infrared stereo scene camera 510 may detect infrared light reflected off the exterior of eye 300 into right lens 511*a* and left lens 511*b* and send a signal corresponding to the detected infrared light to processor 135. Processor 135 may execute instructions to produce infrared lower magnification right-eye-view image 531*a* and infrared lower magnification left-eye-view image 531*b*. Processor 135 may execute instructions to combine infrared lower magnification right-eye-view image 531*a* and infrared lower magnification left-eye-view image 531*b* to produce stereoscopic infrared lower magnification digital image of the eye 541. Stereoscopic infrared lower magnification digital image of the eye 541 may be displayed on multiple picture-in-picture display 140, and may be displayed in inset position 241. Multiple picture-in-picture display 140 may display stereoscopic infrared lower magnification digital image of the eye 541 and a main camera digital image of the eye, which may be higher magnification digital image of the eye 142, concurrently. Stereoscopic infrared lower magnification digital image of the eye 541 may allow a surgeon to perform a surgical task at lower magnification and without use of an external illumination source, which may include inserting or removing surgical instruments 101*a* and 101*b* from eye 300, or for example inserting tools into cannulas.

Right infrared scene camera 510*a* may include right lens 511*a* and left infrared scene camera 510*b* may include left lens 511*b*. Right infrared scene camera 510*a* and left infrared scene camera 510*b* may be two separate physical cameras. Alternatively, right infrared scene camera 510*a* and left infrared scene camera 510*b* may be combined into a single physical stereo scene camera. Right lens 511*a* and left lens 511*b* may be fixed focal length lenses, which may have the same focal length. Right infrared scene camera 510*a* may include right infrared image sensor 515*a* and left infrared scene camera 510*b* may include left infrared image sensor 515*b*. Right infrared image sensor 515*a* and left infrared image sensor 515*b* may be photodetectors that detect infrared light. Right infrared image sensor 515*a* and left infrared image sensor 515*b* may be active infrared image sensors, uncooled infrared image sensors, infrared sensitive CMOS sensors, or any combination thereof.

Right lens 511*a* may be positioned appropriately such that right infrared scene camera 510*a* may detect infrared light reflected off the exterior of eye 300 using right infrared image sensor 515*a*, which may send a signal corresponding to the detected infrared light to processor 135 to produce infrared lower magnification right-eye-view image 531*a*. Left lens 511*b* may be positioned appropriately such that left infrared scene camera 510*b* may detect infrared light reflected off the exterior of eye 300 using left infrared image sensor 515*b*, which may send a signal corresponding to the detected infrared light to processor 135 to produce infrared lower magnification left-eye-view image 531*b*. Processor 135 may execute instructions to combine infrared lower magnification right-eye-view image 531*a* and infrared lower magnification left-eye-view image 531*b* to produce stereoscopic infrared lower magnification digital image of the eye 541. The distance between right lens 511*a* and left lens 511*b* may be approximately the intra-ocular distance, or may be approximately 5-10 mm. Infrared stereo scene camera 510 may be mounted on main camera 120, and may be mounted off axis to the surgical view path. Infrared stereo scene camera 510 may be mounted by a ball and socket friction mount, a gooseneck, or a malleable mount.

Alternatively, if right infrared scene camera 510*a* and left infrared scene camera 510*b* are two separate physical cameras, they may be mounted separately on main camera 120. Right infrared scene camera 510*a* may be mounted on main camera 120 by mount 150*a*, and left infrared scene camera 510*b* may be mounted on main camera 120 by mount 150*b*. Right infrared scene camera 510*a* and left infrared scene camera 510*b* may be mounted off axis to the surgical view path. Mounts 150*a* and 150*b* may be ball and socket friction mounts, goosenecks, or malleable mounts.

Figure 6:
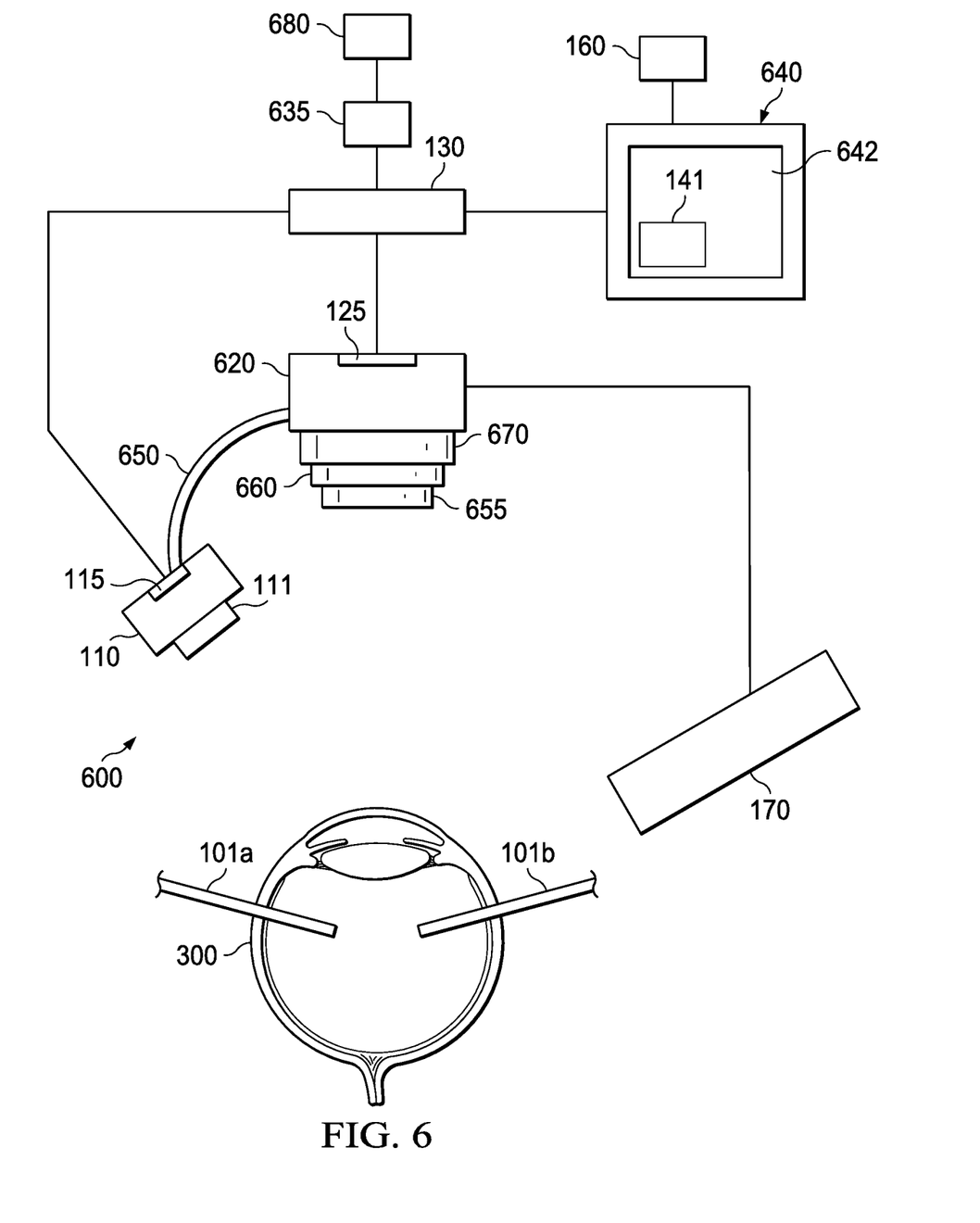
FIG. 6 is a schematic representation of a scene camera system as a component of the NGENUITY® 3D Visualization System (Novartis AG Corp., Switzerland)

Scene camera system 100 may be used as a component of the NGENUITY® 3D Visualization System (Novartis AG Corp., Switzerland) in visualization system 600 as depicted in FIG. 6. For instance, main camera 620 may be a 3D HDR camera and multiple picture-in-picture display 640 may be a 3D 4K OLED surgical display. Multiple picture-in-picture display 640 may display a 3D surgical image of higher magnification digital image of the eye 642. Processor 635 may be an ultra-high-speed 3D image processor, which may optimize 3D HDR images in real time. Visualization system 600 may also utilize optomechanical focus system 655, zoom system 660, variable working distance 670 and software 680. Scene camera 110 may also be a stereo scene camera such as stereo scene camera 310, an infrared scene camera such as infrared scene camera 410, or infrared stereo scene camera 510. Scene camera 110 may be mounted on visualization system 600 using mount 650, and may be mounted off axis to the surgical view path. Mount 650 may be a ball and socket friction mount, a gooseneck, or a malleable mount. Scene camera 110 may be mounted on main camera 620, or may be mounted on another part of visualization system 600.

Figure 7:
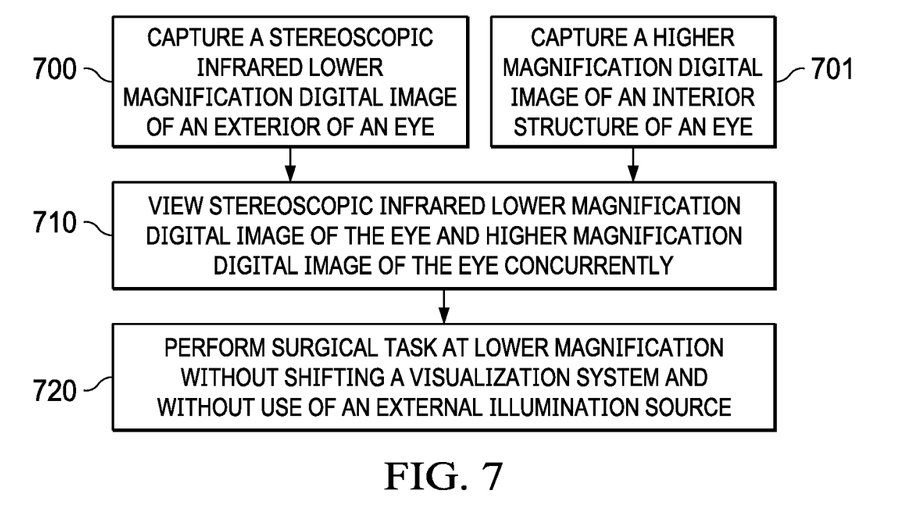
FIG. 7 is a flow chart of a method for performing a surgical task at lower magnification while preserving surgeon dark adaptation during vitreoretinal surgery.

FIG. 7 presents a flow chart for a method of performing a surgical task at lower magnification while preserving surgeon dark adaptation during vitreoretinal surgery. In step 700, an infrared stereo scene camera such as infrared stereo scene camera 510 is used to capture a stereoscopic infrared lower magnification digital image of an eye without use of an external illumination source. The stereoscopic infrared lower magnification digital image of the eye may be a stereoscopic infrared lower magnification digital image of the exterior of the eye. In step 701, a main camera such as main camera 120 is used to capture a higher magnification digital image of the eye, which may be a higher magnification digital image of an interior structure of the eye. In step 710, a multiple picture-in-picture display such as multiple picture-in-picture display 140 is used to view the stereoscopic infrared lower magnification digital image of the eye and the higher magnification digital image of the eye concurrently. In step 720, a surgeon performs a surgical task at lower magnification without shifting a visualization system from viewing a higher magnification digital image of the eye to viewing a lower magnification digital image of the eye and without use of an external illumination source.

Scene camera system 100, multiple picture-in-picture display 140, stereo scene camera 310, infrared scene camera 410, infrared stereo scene camera 510, visualization system 600, and components thereof may be combined with other elements of visualization tools and systems described herein unless clearly mutually exclusive. For instance, infrared stereo scene camera 510 may be combined with visualization system 600, and may be used with other scene camera systems described herein.

The above disclosed subject matter is to be considered illustrative, and not restrictive, and the appended claims are intended to cover all such modifications, enhancements, and other embodiments which fall within the true spirit and scope of the present disclosure. For example, although a scene camera system is most commonly needed to improve visualization during vitreoretinal surgery, if it were useful in another procedure, such as a purely diagnostic procedure not otherwise considered to be surgery, the systems and methods described herein may be employed.

The invention claimed is:

1. A scene camera system comprising:
    an infrared scene camera comprising a lens and operable to detect infrared light reflected off an exterior of an eye into the lens and send a signal corresponding to the detected light to a processor;
    a main camera operable to detect light reflected off an interior structure of the eye and send a signal corresponding to the detected light to the processor;
    an image processing system comprising the processor and operable to execute instructions to produce a scene camera digital image of the eye and a main camera digital image of the eye;
    wherein the infrared scene camera digital image of the eye is an infrared lower magnification digital image of the eye and the main camera digital image of the eye is a higher magnification digital image of the eye; and
    a multiple picture-in-picture display operable to display the scene camera digital image of the eye and the main camera digital image of the eye concurrently,
    wherein the multiple picture-in-picture display is operable to display the infrared lower magnification digital image of the eye and the higher magnification digital image of the eye concurrently.

2. The scene camera system of claim 1, wherein the lens is a fixed focal length lens, an opto-mechanical focus lens, a manual focus lens, or any combination thereof.

3. The scene camera system of claim 1, wherein the scene camera detects light reflected off the exterior of the eye using an image sensor that is a charge-coupled device (CCD) sensor, a complementary metal-oxide semiconductor (CMOS) sensor, a monochrome image sensor, a color image sensor, or any combination thereof.

4. The scene camera system of claim 1, wherein the lens is a fixed focal length lens, an opto-mechanical focus lens, a manual focus lens, or any combination thereof.

5. The scene camera system of claim 1, further comprising an active infrared illuminator.

6. The scene camera system of claim 1, wherein the infrared lower magnification digital image of the eye is produced without use of an external illumination source.

7. The scene camera system of claim 1, wherein the infrared scene camera detects infrared light reflected off the exterior of the eye using an infrared image sensor that is an active infrared image sensor, an uncooled infrared image sensor, an infrared sensitive CMOS sensor, or any combination thereof.

8. The scene camera system of claim 1, wherein the multiple picture-in-picture display is displayed on a digital display, a screen, a head up display, a head mounted display, or any combination thereof.

9. The scene camera system of claim 1, wherein the scene camera is mounted by a ball and socket friction mount, a gooseneck, or a malleable mount.

10. The scene camera system of claim 1, wherein the scene camera is mounted on the main camera.

11. The scene camera system of claim 1, wherein the scene camera has a view path at an oblique angle to a surgical view path.

12. The scene camera system of claim 1, wherein the scene camera system is a component of a NGENUITY® 3D Visualization System.

13. The scene camera system of claim 1, wherein the scene camera digital image of the eye is a lower magnification digital image of the eye and the main camera digital image of the eye is a higher magnification digital image of the eye.

14. The scene camera system of claim 1, wherein the scene camera is a stereo scene camera further operable to detect light reflected off the exterior of the eye into a right lens and a left lens;
wherein the processor is further operable to:
execute instructions to produce a lower magnification right-eye-view image and a lower magnification left-eye-view image;
execute instructions to combine the lower magnification right-eye-view image and the lower magnification left-eye view image to produce a stereoscopic lower magnification digital image of the eye;
wherein the scene camera digital image of the eye is the stereoscopic lower magnification digital image of the eye and the main camera digital image of the eye is a higher magnification digital image of the eye; and
wherein the multiple picture-in-picture display is operable to display the stereoscopic lower magnification digital image of the eye and the higher magnification digital image of the eye concurrently.

15. The scene camera system of claim 14, wherein the right lens and the left lens are fixed focal length lenses.

16. The scene camera system of claim 1, wherein the scene camera is an infrared stereo scene camera further operable to detect infrared light reflected off the exterior of the eye into a right lens and a left lens;
wherein the processor is further operable to:
execute instructions to produce an infrared lower magnification right-eye-view image and an infrared lower magnification left-eye-view image;
execute instructions to combine the infrared lower magnification right-eye-view image and the infrared lower magnification left-eye view image to produce a stereoscopic infrared lower magnification digital image of the eye;
wherein the scene camera digital image of the eye is the stereoscopic infrared lower magnification digital image of the eye and the main camera digital image of the eye is a higher magnification digital image of the eye; and
wherein the multiple picture-in-picture display is operable to display the stereoscopic infrared lower magnification digital image of the eye and the higher magnification digital image of the eye concurrently.

17. The scene camera system of claim 16, wherein the right lens and the left lens are fixed focal length lenses.

18. A scene camera system comprising:
a stereo scene camera comprising a lens and operable to detect light reflected off an exterior of an eye into a right lens and a left lens and send a signal corresponding to the detected light to a processor;
a main camera operable to detect light reflected off an interior structure of the eye and send a signal corresponding to the detected light to the processor;
an image processing system comprising the processor and operable to:
execute instructions to produce a scene camera digital image of the eye and a main camera digital image of the eye;
execute instructions to produce a lower magnification right-eye-view image and a lower magnification left-eye-view image;
execute instructions to combine the lower magnification right-eye-view image and the lower magnification left-eye view image to produce a stereoscopic lower magnification digital image of the eye; and
a multiple picture-in-picture display operable to display the scene camera digital image of the eye and the main camera digital image of the eye concurrently,
wherein the scene camera digital image of the eye is the stereoscopic lower magnification digital image of the eye and the main camera digital image of the eye is a higher magnification digital image of the eye; and
wherein the multiple picture-in-picture display is operable to display the stereoscopic lower magnification digital image of the eye and the higher magnification digital image of the eye concurrently.

* * * * *